(12) United States Patent
Asai

(10) Patent No.: US 12,136,487 B2
(45) Date of Patent: Nov. 5, 2024

(54) MEDICAL IMAGING SYSTEM, MEDICAL IMAGING METHOD, AND IMAGE PROCESSING DEVICE

(71) Applicant: Sony Group Corporation, Tokyo (JP)

(72) Inventor: Atsushi Asai, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 366 days.

(21) Appl. No.: 17/774,858

(22) PCT Filed: Nov. 6, 2020

(86) PCT No.: PCT/JP2020/041553
§ 371 (c)(1),
(2) Date: May 6, 2022

(87) PCT Pub. No.: WO2021/095659
PCT Pub. Date: May 20, 2021

(65) Prior Publication Data
US 2022/0392617 A1 Dec. 8, 2022

(30) Foreign Application Priority Data
Nov. 15, 2019 (JP) ................................ 2019-207358

(51) Int. Cl.
*G16H 30/40* (2018.01)
*G16H 40/20* (2018.01)

(52) U.S. Cl.
CPC ............. *G16H 30/40* (2018.01); *G16H 40/20* (2018.01)

(58) Field of Classification Search
CPC ........ G16H 30/40; G16H 40/20; G16H 20/40; G16H 30/20; G16H 40/63; A61B 1/045
(Continued)

(56) References Cited

U.S. PATENT DOCUMENTS

2007/0236782 A1* 10/2007 Sano .................. G02B 23/2423
359/368
2015/0272694 A1* 10/2015 Charles .................. G16H 40/63
600/202
(Continued)

FOREIGN PATENT DOCUMENTS

JP   2007-275220 A   10/2007
JP   2016-111533 A   6/2016
(Continued)

OTHER PUBLICATIONS

Davison, "Real-Time Simultaneous Localization and Mapping with a Single Camera", Proceedings of the 9th IEEE International Conference on Computer Vision vol. 2, 2003, pp. 1403-1410 (Year: 2003).*

(Continued)

*Primary Examiner* — Juan A Torres
(74) *Attorney, Agent, or Firm* — XSENSUS LLP

(57) ABSTRACT

A surgical medical imaging system includes a second image processing device that acquires a first surgical image signal being a surgical image signal subjected to first image processing, from a medical imaging device including an imaging device and a first image processing device performing the first image processing on the surgical image signal captured by the imaging device, and performs second image processing on the first surgical image signal; and a third image processing device that acquires the first surgical image signal and a second surgical image signal being a surgical image signal subjected to the second image processing, performs third image processing on at least one of the first surgical image signal and the second surgical image signal, and generates a display image signal by conversion processing based on the first and the second surgical image
(Continued)

signals, in which the first, second, and third image processing are different.

15 Claims, 7 Drawing Sheets

(58) Field of Classification Search
USPC .......................................................... 382/128
See application file for complete search history.

(56) References Cited

U.S. PATENT DOCUMENTS

| | | | |
|---|---|---|---|
| 2016/0342847 A1 | 11/2016 | Song et al. | |
| 2018/0110399 A1* | 4/2018 | Mizukami | A61B 1/00105 |
| 2018/0268523 A1* | 9/2018 | Takahasi | A61B 1/015 |
| 2019/0104920 A1* | 4/2019 | Hashimoto | A61B 1/00006 |

FOREIGN PATENT DOCUMENTS

| | | |
|---|---|---|
| JP | 2019-162231 A | 9/2019 |
| WO | 2019/176556 A1 | 9/2019 |

OTHER PUBLICATIONS

International Search Report and Written Opinion mailed on Jan. 19, 2021, received for PCT Application PCT/JP2020/041553, Filed on Nov. 6, 2020, 9 pages including English Translation.

* cited by examiner

MEDICAL IMAGING SYSTEM, MEDICAL IMAGING METHOD, AND IMAGE PROCESSING DEVICE

CROSS-REFERENCE TO RELATED APPLICATIONS

The present application is based on PCT filing PCT/JP2020/041553, filed Nov. 6, 2020, which claims priority to JP 2019-207358, filed Nov. 15, 2019, the entire contents of each are incorporated herein by reference.

FIELD

The present disclosure relates to a medical imaging system, a medical imaging method, and an image processing device.

BACKGROUND

In surgery using a medical imaging device such as an endoscope or a video microscope, it is expected to enable finer manipulation, and further, enable support to the manipulation by using an image processing technology. At this time, the image processing performed on a surgical image signal generated by the medical imaging device is desired to be inhibited from hindering the manipulation. Therefore, in the image processing, for example, real-time performance such as completion of image processing for one frame within a certain period of time, and low latency such as a processing time required for the image processing, that is, a small delay are demanded. In addition, for complex image processing, a large amount of calculation resource is often demanded. Therefore, as image processing becomes more complicated, calculation resources required for the image processing tend to increase.

Incidentally, in an operating room, various medical imaging devices are used, but in some cases, the medical imaging devices do not have a desired image processing function. Therefore, there is provided an IP converter that performs image processing such as rotation correction on a surgical image output from a medical imaging device (e.g., Patent Literature 1).

CITATION LIST

Patent Literature

Patent Literature 1: JP 2019-162231 A

SUMMARY

Technical Problem

According to the conventional art, an IP converter (another image processing device) is used to perform image processing of rotation correction, separately from a medical imaging device.

However, the IP converter is a device for converting signals from a medical device into IP packets, therefore, there is a problem that it is difficult to have calculation capability large enough to perform image processing requiring a large amount of calculation. As described above, in the conventional art, it is impossible to perform the image processing requiring a large amount of calculation. In addition, a plurality of the IP converters is required in the operating room, and from the viewpoint of cost, it is difficult to use an expensive processor such as CPU or GPU. Therefore, in configurations of two image processing devices such as a medical imaging device (an image processing device included therein) and an IP converter (the another image processing device) as provided in the conventional art, it may be difficult to perform desired image processing, and it is not always possible to appropriately generate an image to be displayed. Therefore, a system configuration and an apparatus that enable more flexible image processing are desired.

Therefore, the present disclosure proposes a medical imaging system, a medical imaging method, and an image processing device that are configured to appropriately generate an image to be displayed, by image processing functions distributed to devices.

Solution to Problem

According to the present disclosure, a medical imaging system includes a second image processing device that acquires a first surgical image signal being a surgical image signal subjected to first image processing, from a medical imaging device including an imaging device and a first image processing device performing the first image processing on the surgical image signal captured by the imaging device, and performs second image processing on the first surgical image signal; and a third image processing device that acquires the first surgical image signal and a second surgical image signal being a surgical image signal subjected to the second image processing, performs third image processing on at least one of the first surgical image signal and the second surgical image signal, and generates a display image signal by conversion processing based on the first surgical image signal and the second surgical image signal, wherein the first image processing, the second image processing, and the third image processing are different image processing.

DESCRIPTION OF EMBODIMENTS

Figure 1:
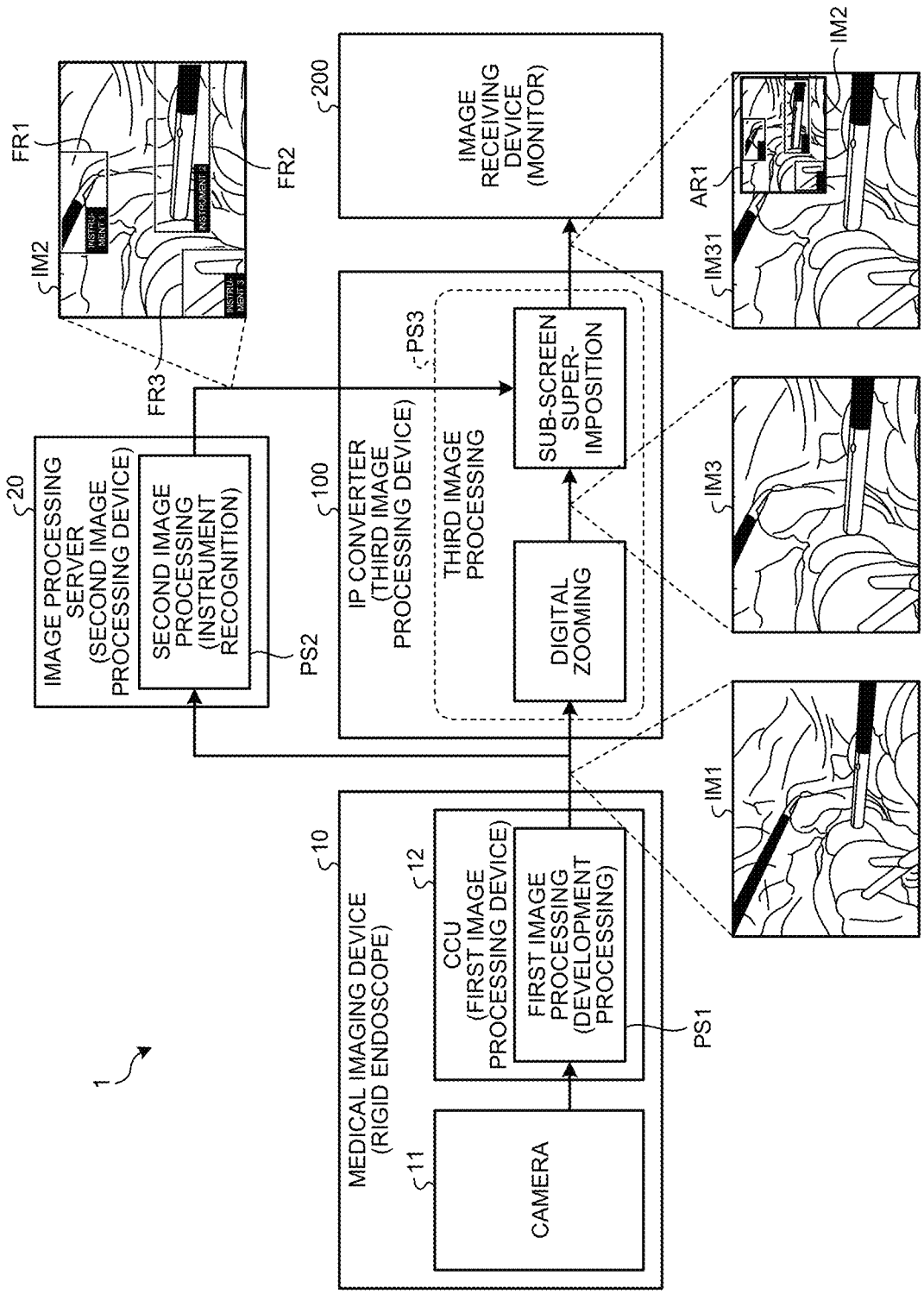
FIG. 1 is a diagram illustrating an example of a configuration of a medical imaging system according to an embodiment of the present disclosure and a process performed thereby.

The embodiments of the present disclosure will be described in detail below with reference to the drawings.

Note that a medical imaging system, a medical imaging method, and an image processing device according to the present application are not limited to these embodiments. Note that in the following embodiments, the same portions are denoted by the same reference numerals or symbols, and repetitive description thereof will be omitted.

Furthermore, the present disclosure will be described in the order of items shown below.

1. Embodiment
1-1. Overview of configuration of medical imaging system according to embodiment of present disclosure and process performed thereby
1-1-1. First to third image processing and the like
1-1-2. Component elements of medical imaging system
1-2. Example of specific configuration of medical imaging system according to embodiment
1-3. Configuration of medical imaging system according to conventional example
1-4. Comparison with conventional system, and effects
1-5. Configuration of IP converter as example of third image processing device
1-6. Procedure of process related to third image processing device
1-7. Procedure of process related to medical imaging system
1-8. Arrangement example of component elements of medical imaging system
2. Other embodiments
2-1. Modifications
2-2. Others
3. Effects according to present disclosure
4. Hardware configuration 1. Embodiment

[1-1. Overview of Configuration of Medical Imaging System According to Embodiment of Present Disclosure and Process Performed Thereby]

FIG. 1 is a diagram illustrating an example of a configuration of a medical imaging system according to an embodiment of the present disclosure and a process performed thereby. As illustrated in FIG. 1, the process according to the embodiment of the present disclosure is implemented by a medical imaging system 1 including an image processing server 20 that is a second image processing device and an Internet Protocol (IP) converter 100 that is a third image processing device. Note that hereinafter, image processing performed by a camera control unit (CCU) 12 that is a first image processing device will be referred to as "first image processing". Image processing performed by the image processing server 20 as the second image processing device will be referred to as "second image processing". Furthermore, image processing performed by the IP converter 100 as the third image processing device is referred to as "third image processing".

Prior to the description of the processing illustrated in FIG. 1, the overview of the medical imaging system 1 illustrated in FIG. 1 will be described. The medical imaging system 1 illustrated in FIG. 1 includes a medical imaging device 10, the image processing server 20, the IP converter 100, and an image receiving device 200. The devices included in the medical imaging system 1 are communicably connected in a wired or wireless manner via a predetermined communication network (e.g., a network N in FIG. 4). Note that the medical imaging system 1 illustrated in FIG. 1 may include a plurality of medical imaging devices 10, a plurality of image processing servers 20, a plurality of IP converters 100, or a plurality of image receiving devices 200.

The medical imaging device 10 functions as an image transmission device. For example, the medical imaging device 10 is also referred to as a modality and is an apparatus used for medical purposes. In the example of FIG. 1, a rigid endoscope including a camera head and the CCU is illustrated as an example of the medical imaging device 10, but the medical imaging device 10 is not limited to the endoscope and may be any of various medical devices such as a surgical camera and a microscope. In other words, the medical imaging device 10 is not limited to the endoscope, is preferably any device having a function of capturing an image, and the configuration thereof is not particularly limited.

The medical imaging device 10 includes a camera 11 (imaging device) with an imaging unit such as an image sensor (camera sensor), and the CCU 12. The medical imaging device 10 has a function of imaging by the camera 11. In the medical imaging device 10, various targets such as biological tissue are imaged by the camera 11. For example, the medical imaging device 10 images a surgical target site. The camera 11 of the medical imaging device 10 generates a surgical image signal by imaging. The camera 11 and the CCU 12 are connected by a signal cable, and the surgical image signal is transmitted from the camera 11 to the CCU 12. The medical imaging device 10 performs the first image processing by using the CCU 12 on input data from the camera 11. Note that, in a case where the medical imaging device 10 is the rigid endoscope, the camera 11 corresponds to the camera head of the rigid endoscope.

The CCU 12 is the first image processing device. The CCU 12 is an image processing device (computer) that performs the first image processing on the surgical image signal generated by the camera 11. For example, the CCU 12 performs the first image processing as basic image processing (development processing) such as demosaicing, noise removal, various distortion correction, and gamma correction. The CCU 12 is arranged in an operating room (see FIG. 7). The CCU 12 performs the processing by an input via a touch panel or a button provided at the CCU, or performs the processing on the basis of a control command acquired from another device (e.g., client terminal).

For example, the CCU 12 includes a communication unit, a storage unit, and a control unit. The communication unit of the CCU 12 is implemented by, for example, a network interface card (NIC), and transmits and receives information to and from the another device, such as the image processing server 20, the IP converter 100, the image receiving device 200, or the client terminal (not illustrated). The storage unit of the CCU 12 is implemented by, for example, a semiconductor memory device such as a random access memory (RAM) or flash memory, or a storage device such as a hard disk or optical disk. The storage unit stores various information for performing the first image processing. For example, the storage unit stores specific processing contents of the first image processing and a program (first image processing program) for performing the first image processing. The control unit of the CCU 12 is implemented by executing a program (e.g., a first image processing program according to the present disclosure) stored in the CCU 12 by, for example, a central processing unit (CPU), a micro processing unit (MPU), or the like, with the random access memory (RAM) or the like as a working area. In addition, the control unit of the CCU 12 is preferably implemented by a circuit, and the function of the CCU 12 may be implemented by an integrated circuit such as an application specific integrated circuit (ASIC) or a field programmable gate array (FPGA).

The CCU 12 is connected to the camera to perform the first image processing on the surgical image signal generated by the camera. As illustrated in FIG. 1, the CCU 12 is provided in the medical imaging device 10, is connected to the camera 11, and performs the first image processing on the surgical image signal captured by the camera 11.

The image processing server 20 is the second image processing device. The image processing server 20 is an image processing device (computer) that performs the second image processing. The image processing server 20 is a server device that is arranged outside the operating rooms and connected to a plurality of IP converters 100 arranged in different operating rooms via an IP switch and the network (see FIG. 7). The image processing server 20 is the image processing device other than the CCUs 12 and the IP converters 100 arranged in the operating rooms. The image processing server 20 performs processing on the basis of a control command acquired from the another device (e.g., the client terminal).

Note that the arrangement of the image processing server 20 in the medical imaging system 1 is not limited to the form of arrangement outside the operating rooms as described above. For example, the operation form of the image processing server 20 may be an on-premise form in which the image processing server 20 is arranged in the operating room or a facility where the operating room is provided, or may be a cloud form in which the image processing server 20 is arranged outside the operating room or outside the facility where the operating room is provided. In other words, the image processing server 20 in the medical imaging system 1 may be installed at any position as long as the conditions of the operation of the medical imaging system 1 are satisfied. However, in a case where the image processing server 20 is provided outside the operating room, a large cooling facility or the like that cannot be installed in the operating room can be used, thus improving the performance of the image processing server.

For example, the image processing server 20 includes a communication unit, a storage unit, and a control unit. The communication unit of the image processing server 20 is implemented by, for example, NIC or the like, and transmits and receives information to and from the another device, such as the medical imaging device 10, the IP converter 100, the image receiving device 200, or the client terminal (not illustrated). The storage unit of the image processing server 20 is implemented by, for example, a semiconductor memory device such as RAM or a flash memory, or a storage device such as a hard disk or optical disk. The storage unit stores various information for performing the second image processing. For example, the storage unit stores specific processing contents of the second image processing and a program (second image processing program) for performing the second image processing. The control unit of the image processing server 20 is implemented by executing a program (e.g., the image processing program such as the second image processing program according to the present disclosure) stored in the image processing server 20 by, for example, CPU, MPU, a graphics processing unit (GPU), or the like, with the RAM or the like as a working area. Furthermore, the control unit is preferably implemented by a circuit, and may be, for example, by an integrated circuit such as ASIC or FPGA. The image processing server 20 performs the processing by an input via a touch panel or a button provided at the image processing server 20, or performs the processing on the basis of the control command acquired from the another device (e.g., the client terminal).

The image processing server 20 acquires a first surgical image signal that is a surgical image signal subjected to the first image processing, and performs the second image processing on the first surgical image signal. The image processing server 20 performs the second image processing requiring an amount of calculation larger than that required for the third image processing. The second image processing is preferably image processing in which the amount of calculation changes depending on the content of an image to be processed. The second image processing employs, for example, simultaneous localization and mapping (SLAM) processing or object recognition processing using machine learning. For example, the image processing server 20 performs, as the second image processing, image processing related to object recognition in which the amount of calculation changes depending on the number of tools included in an image, the size of the image, and the like, on the first surgical image signal.

Furthermore, for example, in a case where the SLAM processing is performed as the second image processing, the image processing server 20 performs the second image processing by using various technologies related to SLAM. In this case, the image processing server 20 performs the SLAM processing on the basis of the first surgical image signal to create a three-dimensional map of environment monitored by the medical imaging device 10 (or the camera 11) and identify the self-position of the camera 11. The SLAM processing uses an algorithm such as any of PTAM, LSD-SLAM, ORB-SLAM, and RGB-D-SLAM, which are the SLAM processing. For example, the image processing server 20 creates internal environment map information (internal three-dimensional information etc.) of the environment (internal body) monitored by the medical imaging device 10 (camera 11) by using a technology related to SLAM, and identifies the self-position of the camera 11. The basic principle of SLAM technology using a monocular camera is described, for example, in "Andrew J. Davison, "Real-Time Simultaneous Localization and Mapping with a Single Camera", Proceedings of the 9th IEEE International Conference on Computer Vision Volume 2, 2003, pp. 1403-1410". Furthermore, the SLAM technology estimating the three-dimensional position of a subject by using a camera image of the subject is also particularly referred to as visual SLAM. Note that, in this configuration, the medical imaging device 10 may include, for example, the camera 11 configured to capture (detect) information necessary to perform the SLAM processing, or a sensor other than the camera 11 necessary to perform the SLAM. For example, an IMU sensor may be provided in addition to the camera 11 to perform the SLAM processing on the basis of the first surgical image signal and a sensor signal from the IMU sensor. Furthermore, the camera 11 may be a monocular camera or a stereo camera.

Furthermore, for example, in a case where the object recognition using the machine learning is performed as the second image processing, the image processing server 20 performs the second image processing by using various technologies related to the machine learning. In this case, the image processing server 20 generates a recognition model for the object recognition by using the technologies related to the machine learning, inputs the first surgical image signal to the generated recognition model, and performs the second image processing. For example, a plurality of surgical image signals each labeled with a feature of the subject is input as learning data to a machine learning algorithm having a multilayer neural network, generating a parameter. Then, the image processing server 20 reads an inference algorithm (e.g., recognition algorithm) having the multilayer neural network adjusted on the basis of the parameter, inputs the first surgical image signal to the inference algorithm, as the second image processing, and outputs a calculated result (e.g., recognition result). Note that the above description is merely an example, and the image processing server 20 may perform the second image processing by using any technology as long as the SLAM or the object recognition using machine learning can be performed.

The image processing server 20 has a plurality of application programs (hereinafter, also referred to as "applications") in the storage unit, and selects an application to be used from the plurality of applications, according to selection designated by the client terminal. For example, the image processing server 20 has a plurality of applications including a first application that performs the SLAM processing and a second application that performs the object recognition, and performs, as the second image processing, image processing corresponding to an application selected by the designation from the client terminal.

The IP converter 100 is a converter that converts an image signal into a signal transmittable according to IP (e.g., Ethernet signal). Preferably, the IP converter is configured to further convert an electrical signal into an optical signal. The IP converter 100 is the third image processing device. The IP converter 100 is an image processing device (computer) that performs the third image processing. For example, the IP converter 100 performs, as the third image processing, at least one of zooming, image stabilization, rotation correction, and picture in picture (PinP). The IP converter 100 performs, as the third image processing, image processing such as zooming, image stabilization, rotation correction, or PinP, by using various technologies. For example, in a case where the image stabilization is performed, the IP converter 100 performs a motion vector extraction processing on a surgical image, and moves the surgical image in an opposite phase to the extracted motion vector, thereby correcting camera shake. The IP converter 100 is arranged in the operating room (see FIG. 7). The IP converter 100 performs the processing on the basis of an input signal, or a control command acquired from the another device (e.g., the client terminal).

The IP converter 100 acquires the first surgical image signal and a second surgical image signal that is a surgical image signal subjected to the second image processing, performs the third image processing on at least one of the first surgical image signal and the second surgical image signal, and generates a display image signal by conversion processing based on both of the first surgical image signal and the second surgical image signal.

The IP converter 100 performs the third image processing on the basis of a result of the second image processing by the image processing server 20. The IP converter 100 performs the third image processing on a third surgical image signal obtained by superimposing the second surgical image signal on the first surgical image signal. The IP converter 100 performs the third image processing based on the selected application, in response to an instruction from the client terminal. The IP converter 100 changes the contents of the third image processing on the basis of the type of the second image processing. The IP converter 100 performs the third image processing corresponding to the second image processing of the selected application. When the image processing server 20 does not respond, the IP converter 100 sets the first surgical image signal as the display image signal.

The image receiving device 200 is a device that receives an image from an external device. The image receiving device 200 is a device that displays and records the image received from the external device. The example of FIG. 1 illustrates the image receiving device 200 that is a monitor. However, the image receiving device 200 is not limited to the monitor, and may be any of various devices such as a display device displaying an image and a device (image management server) such as a storage device recording an image. For example, the image receiving device 200 may be a display or a projector other than the monitor as the display device, a recorder as a storage device, or the like. The image receiving device 200 receives the image signal (image) output from the IP converter 100. The image receiving device 200 receives the image signal (image) transmitted from the IP converter 100.

Hereinafter, the processing illustrated in FIG. 1 will be specifically described. In the example of FIG. 1, the medical imaging device 10 that is the rigid endoscope will be exemplified.

First, the camera 11 of the medical imaging device 10 performs image capturing. The camera 11 transmits the surgical image signal captured to the CCU 12 that is the first image processing device. Then, the CCU 12 performs the first image processing PS1 on the surgical image signal acquired from the camera 11. For example, the CCU 12 generates the first surgical image signal corresponding to a surgical image IM1 illustrated in FIG. 1 by the first image processing PS1 as the development processing.

Then, the CCU 12 transmits the first surgical image signal to the image processing server 20 that is the second image processing device. The first surgical image signal corresponds to the surgical image IM1 illustrated in FIG. 1. The image processing server 20 performs the second image processing PS2 on the first surgical image signal corresponding to the surgical image IM1. In the example of FIG. 1, the image processing server 20 performs the second image processing PS2 as the object recognition (instrument recognition). The image processing server 20 recognizes three instruments included in an image area of the first surgical image signal by the second image processing PS2 on the first surgical image signal. For example, the CCU 12 generates the second surgical image signal corresponding to a surgical image IM2 illustrated in FIG. 1 by the second image processing PS2 as the instrument recognition. The image processing server 20 generates the second surgical image signal corresponding to the surgical image IM2 including three frames FR1 to FR3 indicating the positions (regions) of the three instruments.

Then, the image processing server 20 transmits the second surgical image signal to the IP converter 100. The image processing server 20 transmits the second surgical image signal corresponding to the surgical image IM2 to the IP converter 100. Furthermore, the CCU 12 transmits the first surgical image signal to the IP converter 100 that is the third image processing device. The CCU 12 transmits the first surgical image signal corresponding to the surgical image IM1 to the IP converter 100. Note that either of the transmission of the second surgical image signal to the IP converter 100 by the image processing server 20 and the transmission of the first surgical image signal to the IP converter 100 by the CCU 12 may be carried out at the early timing, or both of the transmission of the second surgical image signal and the transmission of the first surgical image signal may be carried out at the same timing. Furthermore, a transmission destination of the CCU 12 or the image processing server 20 may be determined by the IP switch.

The IP converter 100 performs the third image processing PS3 by using the first surgical image signal and the second surgical image signal. In the example of FIG. 1, the IP converter 100 digitally zooms the first surgical image signal. The IP converter 100 digitally zooms the first surgical image signal corresponding to the surgical image IM1 to generate a surgical image signal corresponding to a surgical image IM3.

Then, the IP converter 100 performs sub-screen superimposition. The IP converter 100 superimposes the second surgical image signal on the surgical image signal corresponding to the surgical image IM3. In the example of FIG. 1, the IP converter 100 performs image processing of superimposing the second surgical image signal corresponding to the surgical image IM2 on the surgical image signal corresponding to the surgical image IM3. The IP converter 100 performs image processing related to PinP. Therefore, the IP converter 100 generates the display image signal corresponding to a surgical image IM31 in which the surgical image IM2 as a sub-screen including the three frames FR1 to FR3 is superimposed on the surgical image IM3 obtained after the digital zooming. The IP converter 100 generates the display image signal corresponding to the surgical image IM31 obtained by superimposing the surgical image IM2 on a partial region of the surgical image IM3 obtained after the digital zooming. In FIG. 1, the IP converter 100 generates the display image signal corresponding to the surgical image IM31 obtained by superimposing the surgical image IM2 on an upper right area AR1 of the surgical image IM3. As described above, the IP converter 100 generates the display image signal in a PinP manner by combining the two images (videos). In the example of FIG. 1, the IP converter 100 combines the surgical image IM3 and the surgical image IM2 to generate the display image signal in which the surgical image IM2 is displayed on the surgical image IM3 in the PinP manner.

Then, the IP converter 100 transmits the display image signal to the image receiving device 200. In the example of FIG. 1, the IP converter 100 transmits the display image signal corresponding to the surgical image IM31 to the image receiving device 200. Then, the image receiving device 200 displays the surgical image IM31 on a screen.

As described above, in the medical imaging system 1, the CCU 12, the IP converter 100, and the server (image processing server 20) perform different image processing. In the example of FIG. 1, the medical imaging system 1 is configured not to perform image processing by the IP converter 100 on the basis of a result of analysis by the server, but to perform other image processing not involved in the image processing performed by the IP converter 100 by another server (the image processing server 20) different from the IP converter 100. As described above, the medical imaging system 1 is configured so that a function having a high processing load on the IP converter 100, such as image recognition, is performed by the image processing server 20, providing the function via a video network. In other words, the medical imaging system 1 performs image processing requiring a large amount of calculation on the server side such as the image processing server 20, and performs image processing requiring a small amount of calculation on the IP converter side. Therefore, the medical imaging system 1 is configured to appropriately generate an image to be displayed, by image processing functions distributed to the respective devices. In order to analyze the surgical image output from the medical imaging device and implement a desired image processing function, the medical imaging system 1 is configured to perform image processing requiring a large amount of calculation while ensuring real-time performance and low latency. The medical imaging system achieves the image processing requiring the large amount of calculation while ensuring the real-time performance and low latency, for further support to the manipulation.

In addition, the medical imaging system 1 is configured to build a system not depending on a vendor of the medical imaging device 10 such as the endoscope or the image receiving device 200 such as the monitor. Furthermore, with the medical imaging system 1, it is possible to suppress the influence on the basic image processing (development processing) of the CCU 12, due to the image processing functions distributed to the respective devices. In addition, in the medical imaging system 1, the real-time performance and low latency in the image transmission by the IP converter 100 can be maintained, due to the image processing functions distributed to the respective devices. In the medical imaging system 1, the image processing functions distributed to the respective devices readily enhances the performance of the image processing server 20. Therefore, it is possible to flexibly support a network configuration, the increase or decrease of the IP converters as the client, or the change in the function and performance of the image processing.

[1-1-1. First to Third Image Processing and Like]

In the above, the first image processing as the development processing, the second image processing as the SLAM or object recognition, and the third image processing as the zoom processing or superimposition processing have been described, but the first to third image processing may be any of various types of processing. For example, the second image processing may be any processing as long as the amount of calculation is larger than that in the third image processing. Furthermore, the second image processing may be image processing in which the amount of calculation changes depending on the content of the image to be processed. For example, the medical imaging system 1 may determine the second image processing and the third image processing, on the basis of the amount of calculation.

The medical imaging system 1 may determine to cause which one of the second image processing device and the third image processing device to perform which image processing, on the basis of various criteria such as processing time. For example, the medical imaging system 1 may cause the IP converter 100 being the third image processing device to perform, as the third image processing, image processing that can be performed at 60 frames per second (fps) or less on a 4K resolution image. In other words, the medical imaging system 1 may cause the IP converter 100 to perform, as the third image processing, the image processing requiring a small amount of calculation that can be performed at 60 fps on the 4K resolution image. In addition, for example, the medical imaging system 1 may cause the image processing server 20 as the second image processing device to perform, as the second image processing, image processing that cannot be performed at 60 fps or less on the 4K resolution image. In other words, the medical imaging system 1 may cause the image processing server 20 to perform, as the second image processing, the image processing requiring a large amount of calculation that is difficult to be performed at 60 fps on the 4K resolution image. As described above, the medical imaging system 1 may determine to cause which image processing device to perform which image processing, on the basis of the number of frames to be processed per unit time.

Note that, as described above, 60 fps is represented as the criterion for the 4K resolution image as an example, but the present disclosure is not limited thereto, and various criteria may be employed. The medical imaging system 1 may determine the classification of image processing, for example, by defining the first image processing as the development processing, the third image processing as the zoom processing or superimposition processing, and the second image processing as image processing requiring the amount of calculation larger than that required for the third image processing. Furthermore, for example, the medical imaging system 1 may determine the development processing as the first image processing, and enhancement processing including the recognition processing such as the SLAM or object recognition, super-resolution processing, or the like as the second image processing. In addition, additional processing including the zoom processing or superimposition processing requiring a smaller amount of calculation than that required in the second image processing may be determined as the third image processing. Note that the above description is merely an example, and classification of the image processing into which of the first image processing, the second image processing, and the third image processing may be determined on the basis of various criteria according to the use, purpose, and the like.

Furthermore, the first image processing to third image processing are not limited to the processing contents or process procedure as illustrated in FIG. 1, and may employ various processing. For example, the image processing server 20 may generate a surgical image (surgical image IM22) in which only the frames FR1 to FR3 indicating the positions of the instruments are arranged as a result of the object recognition by the second image processing. Then, the IP converter 100 may acquire the surgical image IM22 from the image processing server 20 to perform image processing of superimposing the surgical image IM22 on the surgical image IM1 acquired from the CCU 12. Therefore, the IP converter 100 may generate a surgical image IM41 in which the surgical image IM22 is superimposed on the surgical image IM1. Furthermore, the IP converter 100 may perform zoom processing on the surgical image IM41 to generate a surgical image IM51 that has a desired portion zoomed. Then, the image receiving device 200 may display the surgical image IM51 acquired from the IP converter 100. Furthermore, in a case where the second image processing by the image processing server 20 is SLAM, the IP converter 100 performs image processing corresponding to the SLAM, as the third image processing. For example, the IP converter 100 may perform zoom processing to a position estimated by the SLAM, as the third image processing. Note that the above descriptions are merely examples, and the medical imaging system 1 is not limited to the above descriptions, and may perform various combinations of the first to third image processing.

[1-1-2. Component Elements of Medical Imaging System]

In addition, the medical imaging system 1 is not limited to the component elements described above, and may include various component elements.

For example, the medical imaging system 1 may include the another device that transmits a control command (control information) for controlling at least one of the first image processing device, the second image processing device, and the third image processing device, to the at least one device. In this configuration, for example, the another device, such as the client terminal or a control panel, transmits the control command for controlling the performance of the processing or the like, to the CCU 12, the image processing server 20, or the IP converter 100. Therefore, in the CCU 12, the image processing server 20, or the IP converter 100, the processing is controlled according to the control command received from the another device.

Furthermore, for example, the medical imaging system 1 may include the client terminal that designates an application to be performed, from among the plurality of applications included in the second image processing device. For example, the medical imaging system 1 may include the client terminal that designates an application to be run, from among the first application performing the SLAM and the second application performing the object recognition that are included in the image processing server 20. In this configuration, the client terminal transmits information (designation information) indicating the application designated by the user (user) to the image processing server 20, and the image processing server 20 that has received the designation information performs the second image processing by using the designated application.

In addition, the third image processing device performs the third image processing based on the selected application, in response to the instruction from the client terminal. The IP converter 100 performs the third image processing corresponding to the application run by the image processing server 20. In a case where the image processing server 20 performs the image processing related to the object recognition, as the second image processing, the IP converter 100 performs image processing corresponding to the object recognition, as the third image processing. For example, in a case where the image processing server 20 performs the image processing related to the object recognition as the second image processing, the IP converter 100 performs image processing for superimposing a result of the object recognition on the first surgical image signal, as the third image processing.

[1-2. Example of Specific Configuration of Medical Imaging System According to Embodiment]

Figure 2:
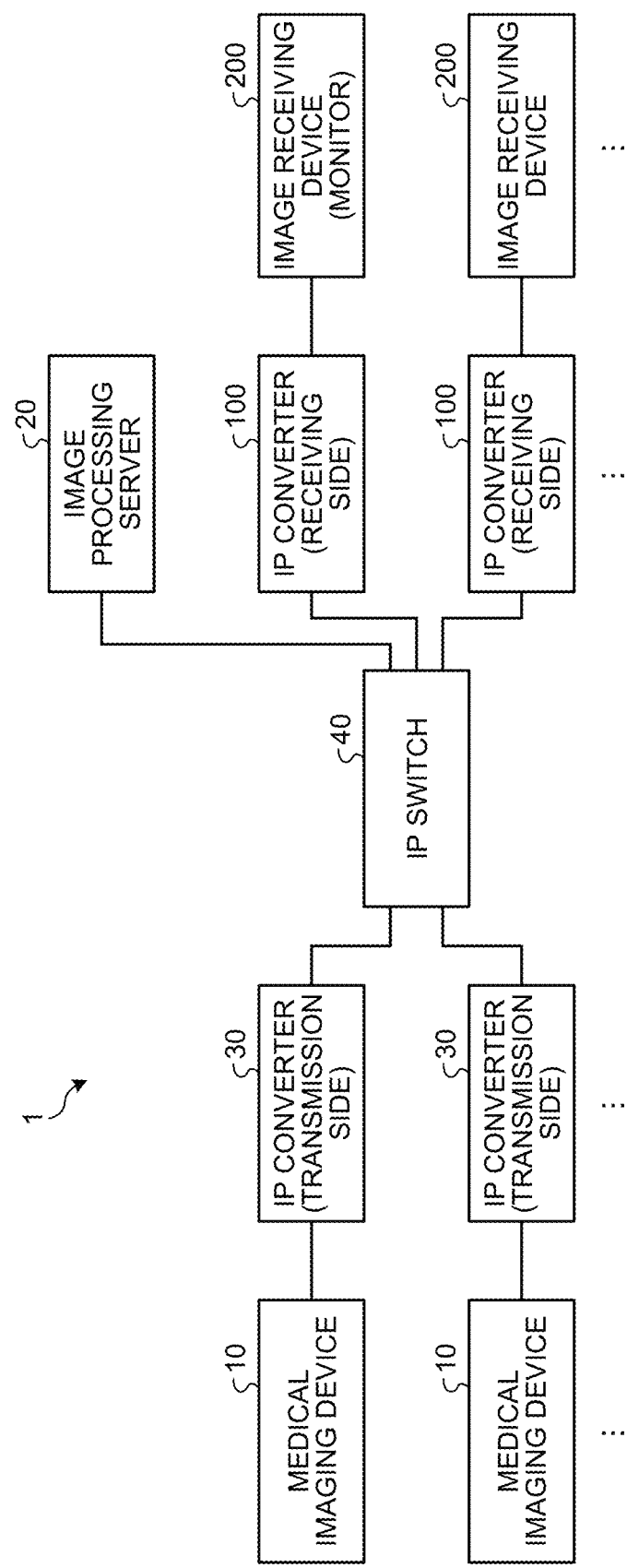
FIG. 2 is a diagram illustrating a specific configuration example of the medical imaging system according to the embodiment.

Next, an example of a specific configuration of the medical imaging system 1 will be described with reference to FIG. 2. FIG. 2 is a diagram illustrating a specific configuration example of the medical imaging system according to the embodiment.

The medical imaging system 1 includes a plurality of the medical imaging devices 10, a plurality of IP converters 30 on the transmission side, an IP switch 40, the image processing server 20, a plurality of the IP converters 100 on the reception side, and a plurality of the image receiving devices 200.

An electric signal (surgical image signal) of the surgical image captured by the camera 11 of each of the medical imaging devices 10 is subjected to the first image processing by the CCU 12, then converted into an optical signal by the corresponding IP converter 30, and output to the image processing server 20 or each of the IP converters 100 by the IP switch 40 (optical switcher etc.). For example, each of the IP converters 30 and 100, and the IP switch 40 are connected by an optical fiber cable or the like. Note that unlike the IP converter 100 as the third image processing device, the IP converter 30 does not have the function of performing the third image processing, and only has a function as the IP converter. The IP switch 40 has a function of transmitting a received signal to a predetermined device, on the basis of a command from the external device (e.g., the client terminal).

The image processing server 20 acquires the first surgical image signal subjected to the first image processing by the CCU 12 of each medical imaging device 10, and performs the second image processing on the first surgical image signal. Then, the image processing server 20 transmits the second surgical image signal subjected to the second image processing to each of the IP converters 100.

Each of the IP converters 100 converts the optical signal supplied from the IP switch 40 into an electric signal and supplies the electric signal to a corresponding image receiving device 200. The IP converter 100 acquires the first surgical image signal after the first image processing by the CCU 12 of the medical imaging device 10 and the second surgical image signal after the second image processing by the image processing server 20. Then, the IP converter 100 performs the third image processing on at least one of the first surgical image signal and the second surgical image signal to generate the display image signal by the conversion processing based on the first surgical image signal and the second surgical image signal. Then, the IP converter 100 supplies the generated display image signal to the corresponding image receiving device 200.

Note that the specific configuration of the medical imaging system 1 illustrated in FIG. 2 is an example of the medical imaging system 1, and the medical imaging system 1 is not limited to the configuration illustrated in FIG. 2, and may have various configurations as long as the processing illustrated in FIG. 1 can be implemented.

[1-3. Configuration of Medical Imaging System According to Conventional Example]

Figure 3:
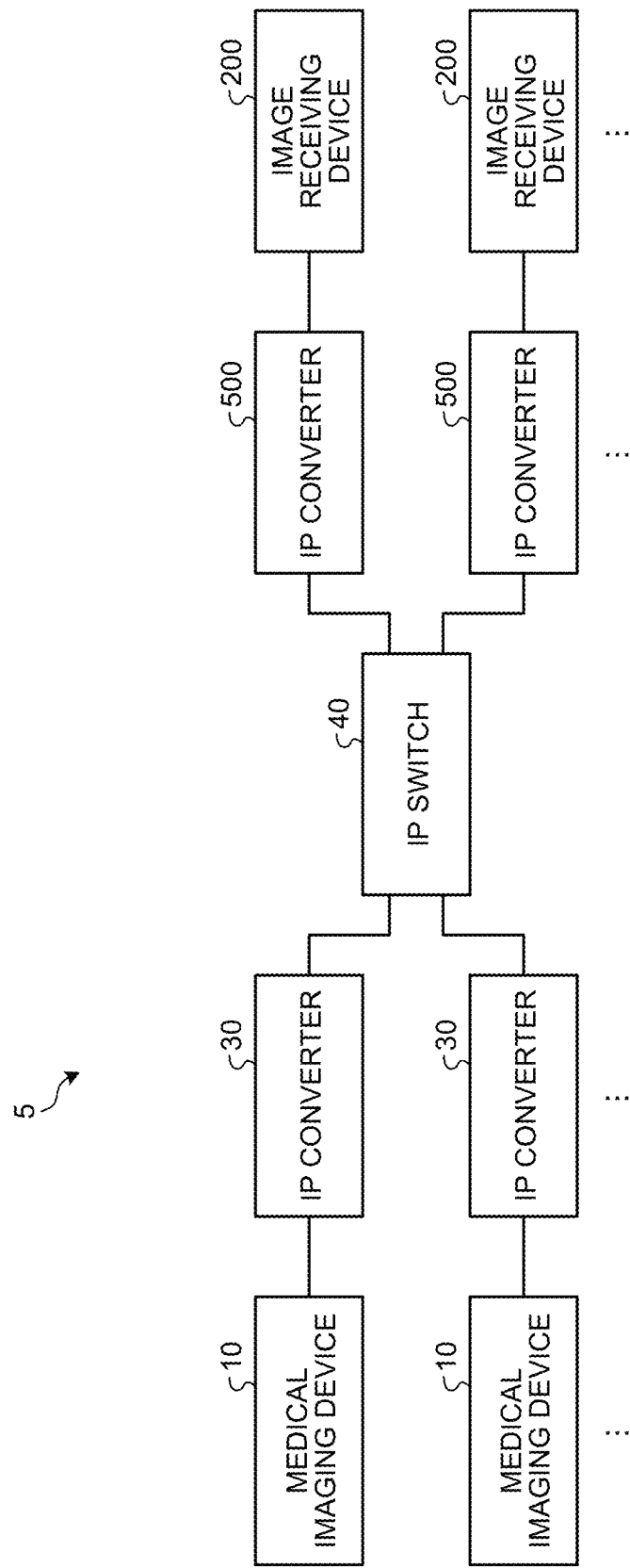
FIG. 3 is a diagram illustrating a configuration example of a medical imaging system according to a conventional example.

Here, a configuration of a medical imaging system according to a conventional example will be described with reference to FIG. 3. FIG. 3 is a diagram illustrating a configuration example of the medical imaging system according to the conventional example. Note that the same points as those in FIG. 2 are denoted by the same reference numerals, and descriptions thereof are appropriately omitted.

A conventional system 5 as a conventional medical imaging system includes a plurality of medical imaging devices 10, a plurality of IP converters 30 on the transmission side, an IP switch 40, a plurality of IP converters 500 on the reception side, and a plurality of image receiving devices 200. Each of the IP converters 500 converts an optical signal supplied from the IP switch 40 into an electric signal and supplies the electric signal to a corresponding image receiving device 200. In addition, the IP converter 500 performs image processing.

As illustrated in FIG. 3, the conventional system 5 includes no server that performs the second image processing. Therefore, in the conventional system 5, a CCU 12 of each medical imaging device 10 or each IP converter 500 on the reception side needs to perform the function of the second image processing. In a case where the IP converter 500 performs the function of the second image processing, the IP converter 500 uses a first surgical image signal after first image processing by the CCU 12 of the medical imaging device 10 to generate a display image signal by the performance of the second image processing and third image processing, and supplies the generated display image signal to the corresponding image receiving device 200.

[1-4. Comparison with Conventional System, and Effects]

Hereinafter, a comparison between the present application and the conventional art, as well as effects of the present application will be described with reference to FIGS. 1 to 3.

In an imaging device (the medical imaging device 10), generally, the basic image processing (development processing) such as demosaicing/noise removal/various distortion corrections/gamma correction is performed on input data from a camera sensor (camera 11) by the CCU 12, and then a video is output to the outside.

An image output from the medical imaging device 10 is displayed on the image receiving device 200 such as a monitor or stored in an external storage. At this time, instead of directly connecting the medical imaging device 10 and the image receiving device 200, a method of connecting the medical imaging device 10 and the image receiving device 200 via the video network in an operating room or hospital is getting common. This is because various videos of an endoscope, an ultrasonic diagnostic apparatus, a biological information monitor, and the like that are used in surgery can be switchably displayed on any monitor.

As described above, particularly, the video networks based on Ethernet (registered trademark) have been widely introduced now due to various merits in view of physical space or the like. In this case, as illustrated in FIG. 2, it is necessary to insert converters (the IP converters 30 and 100) for converting the Ethernet (registered trademark) signal and the inputs/outputs of the medical imaging device 10 and image receiving device 200. As illustrated in FIG. 2, for the inputs/outputs on the side of the medical imaging device 10 and image receiving device 200, a general interface such as a serial digital interface (SDI), a high-definition multimedia interface (HDMI) (registered trademark), or a display port is often used.

In addition to the basic image processing (development processing) performed by the CCU 12 as described above, providing additional image processing such as digital zooming enables to support diagnosis or surgery. Although it is also conceivable that the above processing is performed by the CCU 12, the functions in the CCU 12 are enlarged, leading to an increase in development and quality control costs. Furthermore, similar functions provided for the respective vendors of the devices lead to difference in operability with poor usability. In addition, if the CCU 12 has a failure, there is a possibility that the video is not displayed at worst, even if the failure may occur in an additional function such as digital zooming. Therefore, for example, if a surgical operation is being performed, the failure may suspend the surgical operation, affecting the health and life of the patient. Therefore, both software (SW) and hardware (HW) are preferably separated so that the additional image processing as described above does not affect the basic image processing (development processing).

In view of the above description, it is conceivable that the IP converter 100 achieves the additional function separated as described above. The image that is input from the medical imaging device 10 to the IP converter 100 has a general format such as SDI or HDMI (registered trademark) as described above. Therefore, a function that does not depend on the individual devices or vendors can be achieved, and the function shared between the vendors provides unified operability. Furthermore, even if a problem occurs in the additional function of the IP converter 100 during operation, the IP converter 100 separated from the CCU 12 in terms of HW has a low possibility of affecting the basic image processing (development processing) performed by the CCU 12, and the problem can be avoided by simply turning off the function having the problem in the IP converter 100.

Meanwhile, a problem in the image processing by the IP converter 100 is that the IP converter 100 is generally small in size and has limited calculation capability, and the performance and function of the image processing are limited. In particular, image recognition using machine learning, such as detection of a specific object or situation from an image generally has an increased processing load, and the processing load changes depending on the content of the image. An example of processing similar thereto includes image recognition using the SLAM technology as well. SLAM is a technology for simultaneously performing self-position estimation and environmental map generation from an image, and makes it possible to recognize a three-dimensional shape of an object.

If it is intended to achieve such functions by using the IP converter 100, the performance of a calculator may be insufficient or the real-time performance may be impaired (e.g., causing a problem that the processing is not completed within a certain period of time and late for the drawing timing). On the other hand, it is conceivable to mount a high-performance calculator on the IP converter 100, but the IP converters 100 need to be connected to all devices connected to the video network, thus increasing the cost of the entire system. On the other hand, since the function such as the image recognition is not always used in all devices, there is a possibility that the introduced calculator resource cannot be effectively used.

In view of such a problem, in the medical imaging system 1, the image processing server 20 to perform a function that has a processing load too high to be performed by the IP converter 100 as in the image recognition using the machine learning but that is not always used by all devices is introduced. Thereby the image from the medical imaging device 10 and a result of the processing performed by the server are superimposed and displayed by the IP converter 100. The image processing server 20 is connected to the video network, and runs an application having a high processing load such as the image recognition using the machine learning on demand, on individual images transmitted from one or more imaging devices (medical imaging devices 10).

Therefore, in the example of FIG. 1, an output moving image from the rigid endoscope is transmitted to the video network in the operating room via the IP converter 30 on the transmission side. It is assumed that the IP converter 100 on the reception side digitally zooms this image, and at the same time, the image processing server 20 extracts the instruments used for surgery by the image recognition using the machine learning. Both processing results are superimposed and displayed on the monitor (image receiving device 200) via the IP converter 100 on the reception side.

Furthermore, for example, the image processing server 20 is arranged in or near the operating room and is connected to the network via a switch (such as the IP switch 40). The image processing server 20 receives a moving image transmitted from the rigid endoscope, the same as the image received by the IP converter 100, and extracts the instruments used in the surgery from the image by the image recognition. The image processing server 20 draws rectangles or text in areas of the image from which the instruments are extracted to generate, as a recognition result image, indication of the recognition result, and transmits the recognition result image to the IP converter 100.

Meanwhile, the IP converter 100 receives the recognition result image of the instruments from the image processing server 20, and superimposes and displays the recognition result image as the sub-screen on the digitally zoomed image. The IP converter 100 transmits, as an output image, an image being a result of superimposing and displaying the recognition result image on the digitally zoomed image, to the image receiving device 200. Note that the medical imaging system 1 may set an upper limit of the size of the sub-screen. Therefore, in the medical imaging system 1, the IP converter 100 is allowed to complete the drawing within a certain time period (predetermined threshold).

In addition, although the load, that is, a calculation time in the image processing server 20 depends on the content of a recognition target image, even if the update frequency of result data changes, the IP converter 100 always draws the latest recognition result image, and the change in update frequency does not affect the processing time of the IP converter 100. In other words, the real-time performance and low latency in the image transmission by the IP converter 100 can be maintained.

In the example of FIG. 1, the recognition result image is superimposed after the digital zooming is performed on the IP converter 100. In addition, the image processing server 20 may not be directly connected to the switch (IP switch 40), and the image processing server 20 may be arranged more remotely via another network device. Furthermore, the image processing server 20 can also cover a plurality of operating rooms (see FIG. 7).

It is assumed that the number of clients to which the image processing server 20 provides a function increases depending on the configuration of the network or the number of IP converters 100 connected thereto. Alternately, it is assumed that the image processing function or performance that is performed by the image processing server 20 is changed, requiring further calculation capability. In this case, replacement of the CPU or GPU of the image processing server 20 with a high performance CPU or GPU, or addition of another CPU or GPU to the image processing server 20 makes it possible to readily obtain a necessary performance.

[1-5. Configuration of IP Converter as Example of Third Image Processing Device]

Figure 4:
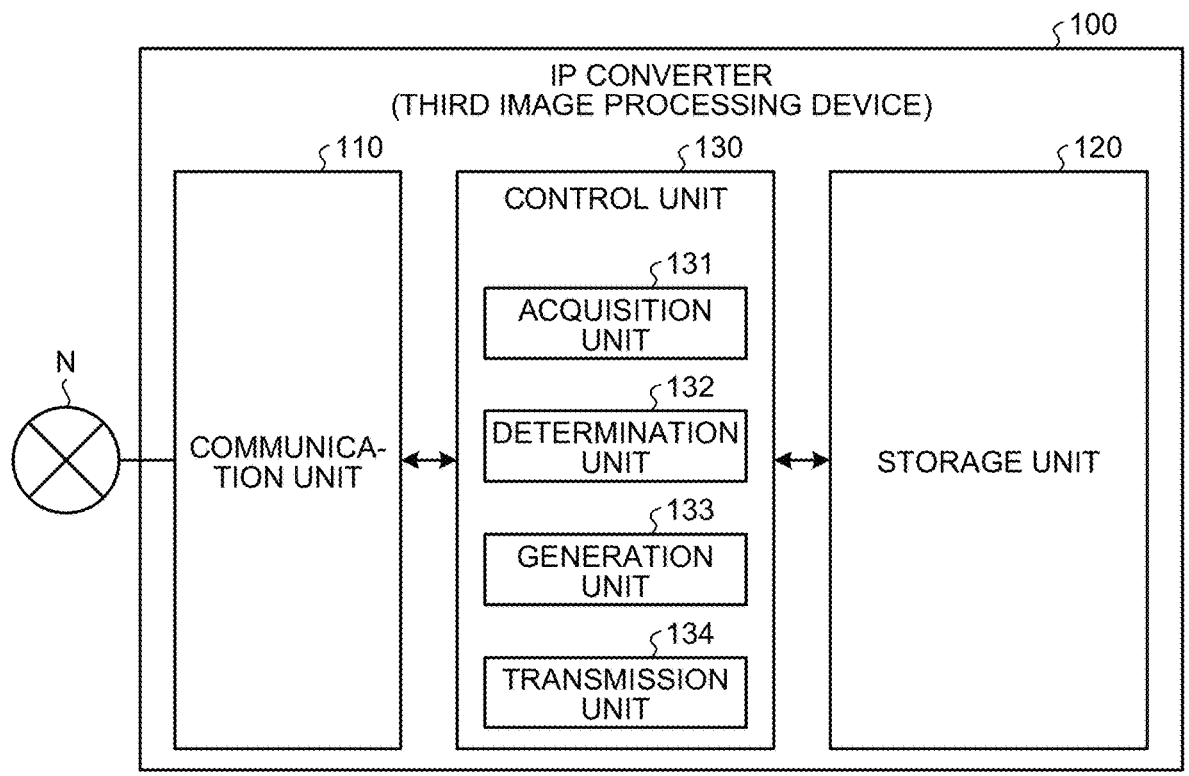
FIG. 4 is a diagram illustrating a configuration example of an IP converter as a third image processing device according to the embodiment.

Next, a configuration of the IP converter as an example of the third image processing device that performs the image processing according to the embodiment will be described. FIG. 4 is a diagram illustrating a configuration example of the IP converter as the third image processing device according to the embodiment.

As illustrated in FIG. 4, the IP converter 100 includes a communication unit 110, a storage unit 120, and a control unit 130. Note that the IP converter 100 may include an input unit (e.g., a keyboard, a mouse, etc.) that receives various operations from an administrator or the like of the IP converter 100, and a display unit (e.g., a liquid crystal display etc.) for displaying various information.

The communication unit 110 is implemented by, for example, NIC or the like. Then, the communication unit 110 is connected to the network N in a wired or wireless manner, and transmits and receives information to and from other information processing devices (computers) such as the medical imaging device 10, the image processing server 20, and the image receiving device 200. Furthermore, the communication unit 110 may transmit and receive information to and from the client terminal (not illustrated).

The storage unit 120 is implemented by, for example, a semiconductor memory device such as RAM or a flash memory, or a storage device such as a hard disk or optical disk. The storage unit 120 according to the embodiment stores various information. The storage unit 120 stores various information for performing the image processing. For example, the storage unit 120 stores specific processing contents of the third image processing and a program (third image processing program) for performing the third image processing. For example, the storage unit 120 may store information indicating a threshold of a time for waiting for a response from the image processing server 20 as the second image processing device.

Returning to FIG. 4, the description will be continued. The control unit 130 is implemented by executing a program (e.g., the image processing program or the like such as the third image processing program or the like according to the present disclosure) stored in the IP converter 100 by, for example, CPU, MPU, or the like, with the RAM or the like as a working area. Furthermore, the control unit 130 is implemented by an integrated circuit such as ASIC or FPGA.

As illustrated in FIG. 4, the control unit 130 includes an acquisition unit 131, a determination unit 132, a generation unit 133, and a transmission unit 134, and implements or performs the function and operation of the image processing described below. Note that the internal configuration of the control unit 130 is not limited to the configuration illustrated in FIG. 4, and may have another configuration as long as image processing described later is performed. Furthermore, a connection relationship between the processing units included in the control unit 130 is not limited to the connection relationship illustrated in FIG. 4, and may have another connection relationship.

The acquisition unit 131 acquires various information. The acquisition unit 131 acquires various information from an external information processing device. The acquisition unit 131 acquires various information from the medical imaging device 10, the image processing server 20, or the image receiving device 200. The acquisition unit 131 acquires various information from the storage unit 120.

The acquisition unit 131 acquires various information determined by the determination unit 132. The acquisition unit 131 acquires various information generated by the generation unit 133.

The acquisition unit 131 acquires the first surgical image signal that is the surgical image signal subjected to the first image processing by the CCU 12. The acquisition unit 131 acquires the second surgical image signal that is the surgical image signal subjected to the second image processing on the first surgical image signal by the image processing server 20.

In the example of FIG. 1, the acquisition unit 131 acquires the first surgical image signal obtained by performing the first image processing by the CCU 12 of the medical imaging device 10 and the second surgical image signal obtained by the second image processing by the image processing server 20. The acquisition unit 131 acquires the first surgical image signal corresponding to the surgical image IM1 and the second surgical image signal corresponding to the surgical image IM2.

The determination unit 132 determines various information. The determination unit 132 discriminates various information. The determination unit 132 determines the various information on the basis of information from the external information processing device. The determination unit 132 determines various information on the basis of information from the other information processing devices such as the medical imaging device 10, the image processing server 20, and the image receiving device 200. The determination unit 132 determines various information on the basis of the information acquired by the acquisition unit 131.

When the image processing server 20 does not respond, the determination unit 132 determines the first surgical image signal as the display image signal. When a time equal to or larger than the predetermined threshold has elapsed since the first surgical image signal was acquired by the acquisition unit 131, the determination unit 132 determines that the image processing server 20 does not respond, and sets the first surgical image signal as the display image signal.

The generation unit 133 generates various information. The generation unit 133 performs information processing such as various image processing. The generation unit 133 performs various image processing. For example, the generation unit 133 performs various information processing on the basis of information from the external information processing device or information stored in the storage unit 120. The generation unit 133 performs various information processing on the basis of information from the other information processing devices such as the medical imaging device 10, the image processing server 20, and the image receiving device 200.

The generation unit 133 performs various information processing on the basis of the various information acquired by the acquisition unit 131. The generation unit 133 performs various information processing on the basis of the various information determined by the determination unit 132. The generation unit 133 performs various information processing on the basis of the various information discriminated by the determination unit 132. The generation unit 133 performs various information processing on the basis of a result of the discrimination by the determination unit 132.

The generation unit 133 performs analysis processing related to the image. The generation unit 133 performs various processing related to the image processing. The generation unit 133 performs processing on image information (image) acquired by the acquisition unit 131. The generation unit 133 performs processing on the image by appropriately using a technology related to the image processing.

The generation unit 133 performs the third image processing on at least one of the first surgical image signal and the second surgical image signal to generate the display image signal by the conversion processing based on the first surgical image signal and the second surgical image signal.

The generation unit 133 performs the third image processing on the basis of a result of the second image processing by the image processing server 20. The generation unit 133 performs the third image processing on the third surgical image signal obtained by superimposing the second surgical image signal on the first surgical image signal. The generation unit 133 performs the third image processing on the basis of the selected application, in response to the instruction from the client terminal. The generation unit 133 changes the contents of the third image processing on the basis of the type of the second image processing. The generation unit 133 performs the third image processing corresponding to the second image processing of the selected application.

The generation unit 133 performs the third image processing including at least one of zooming, image stabilization, rotation correction, or PinP. For example, the generation unit 133 performs, as the third image processing, image processing enabling processing within 60 fps on the 4K resolution image. For example, the generation unit 133 performs, as the third image processing, processing enabling processing within 60 fps on the 4K resolution image, such as zooming, image stabilization, rotation correction, or PinP.

Note that the generation unit 133 may perform image processing by using any technology, as long as desired image processing can be performed, and performs image processing by appropriately using various image processing technologies. The generation unit 133 may perform image processing by appropriately using various information. The generation unit 133 performs various image processing, for example, on an image signal such as raw data acquired from the medical imaging device 10. The image processing include various known signal processing such as development processing, high quality image processing (band enhancement processing, super-resolution processing, noise reduction (NR) processing, and/or image stabilization processing, etc.), and/or enlargement processing (electronic zoom processing). Furthermore, the generation unit 133 performs detection processing on the image signal, for performing AE, AF, and AWB.

In the example of FIG. 1, the generation unit 133 digitally zooms the first surgical image signal. The generation unit 133 digitally zooms the first surgical image signal corresponding to the surgical image IM1 to generate the surgical image signal corresponding to the surgical image IM3. The generation unit 133 performs the sub-screen superimposition. The generation unit 133 superimposes the second surgical image signal on the surgical image signal corresponding to the surgical image IM3. The generation unit 133 performs image processing of superimposing the second surgical image signal corresponding to the surgical image IM2 on the surgical image signal corresponding to the surgical image IM3. The generation unit 133 generates the display image signal corresponding to the surgical image IM31 in which the surgical image IM2 as the sub-screen including the three frames FR1 to FR3 is superimposed on the surgical image IM3 obtained after the digital zooming.

The transmission unit 134 provides various information to the external information processing device. The transmission unit 134 transmits the various information to the external information processing device. For example, the transmission unit 134 transmits various information to the other information processing devices such as the medical imaging device 10, the image processing server 20, and the image receiving device 200. The transmission unit 134 provides information stored in the storage unit 120. The transmission unit 134 transmits the information stored in the storage unit 120.

The transmission unit 134 provides various information on the basis of information from the other information processing devices such as the medical imaging device 10, the image processing server 20, and the image receiving device 200. The transmission unit 134 provides the various information on the basis of the information stored in the storage unit 120.

In the example of FIG. 1, the transmission unit 134 transmits the image IM31 generated by the generation unit 133 to the image receiving device 200. When the image processing server 20 does not respond, the transmission unit 134 transmits the first surgical image signal to the image receiving device 200, as the display image signal. When the first surgical image signal is determined as the display image signal by the determination unit 132, the transmission unit 134 transmits the first surgical image signal to the image receiving device 200.

[1-6. Procedure of Process Related to Third Image Processing Device]

Figure 5:
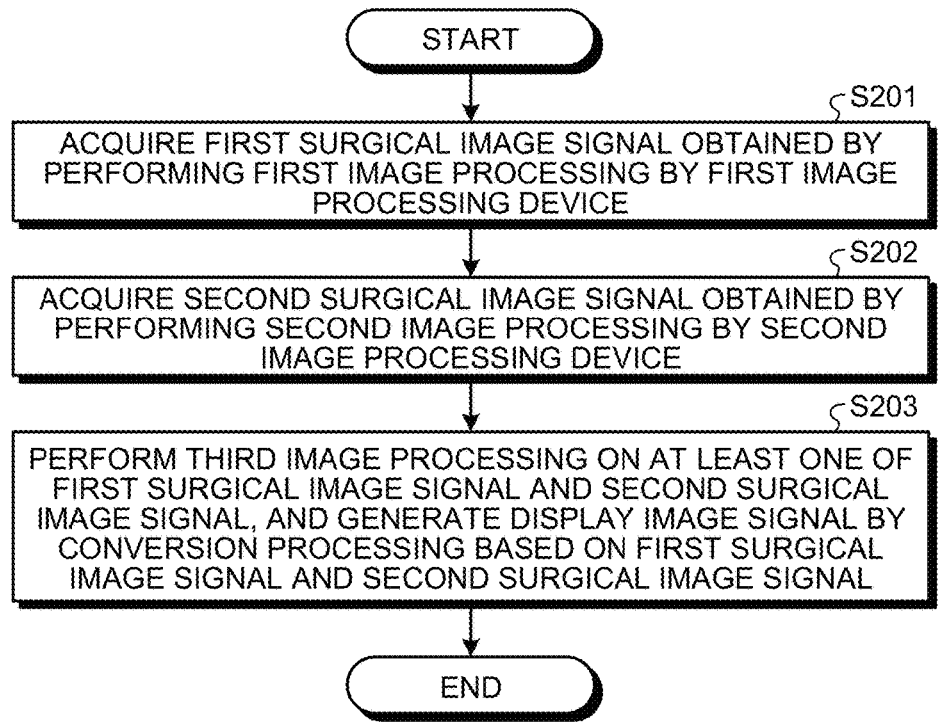
FIG. 5 is a flowchart illustrating a procedure of a process performed by the IP converter as the third image processing device according to the embodiment.

Next, a procedure of processing by the IP converter that is the third image processing device will be described with reference to FIG. 5. FIG. 5 is a flowchart illustrating the procedure of a process performed by the IP converter as the third image processing device according to the embodiment.

As illustrated in FIG. 5, the IP converter 100 acquires the first surgical image signal obtained by performing the first image processing by the first image processing device (Step S101). For example, the IP converter 100 acquires the first surgical image signal from the medical imaging device 10.

The IP converter 100 acquires the second surgical image signal obtained by performing the second image processing by the second image processing device (Step S102). For example, the IP converter 100 acquires the second surgical image signal from the image processing server 20.

The IP converter 100 performs the third image processing on at least one of the first surgical image signal and the second surgical image signal to generate the display image signal by the conversion processing based on the first surgical image signal and the second surgical image signal (Step S103). For example, the IP converter 100 performs the third image processing of superimposing the second surgical image signal on the first surgical image signal, and generates the display image signal.

[1-7. Procedure of Process Related to Medical Imaging System]

Figure 6:
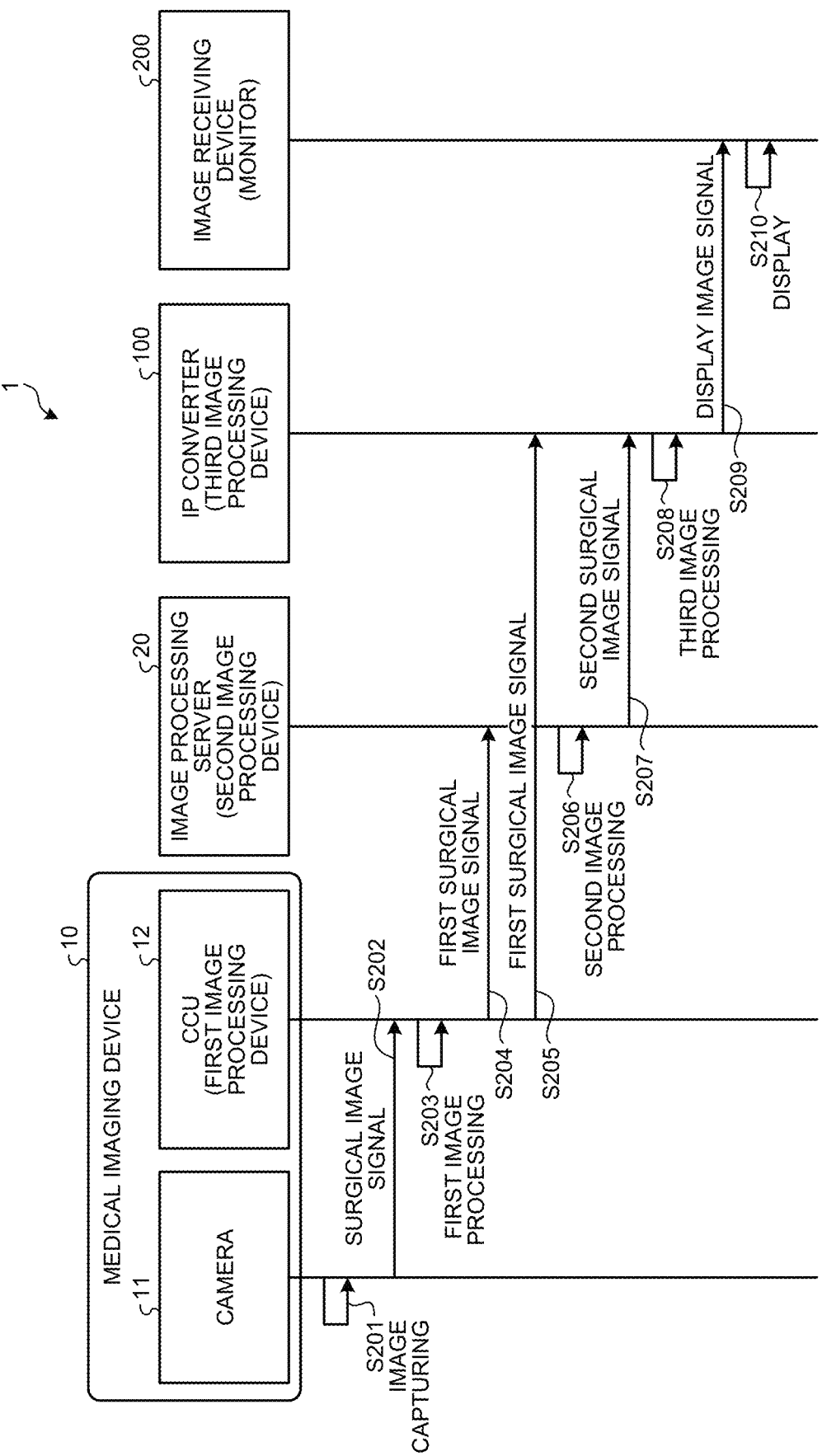
FIG. 6 is a sequence diagram illustrating a process procedure in the medical imaging system according to the embodiment.

Next, the entire process will be described with reference to FIG. 6. FIG. 6 is a sequence diagram illustrating a process procedure in the medical imaging system according to the embodiment.

First, the camera 11 of the medical imaging device 10 performs image capturing (Step S201). Then, the camera 11 transmits the surgical image signal captured to the CCU 12 that is the first image processing device. (Step S202). Thus, the CCU 12 acquires the surgical image signal.

The CCU 12 performs the first image processing on the surgical image signal (Step S203). Thus, the CCU 12 generates the first surgical image signal obtained by performing the first image processing on the surgical image signal.

Then, the CCU 12 transmits the first surgical image signal to the image processing server 20 that is the second image processing device (Step S204). Thus, the image processing server 20 acquires the first surgical image signal.

Furthermore, the CCU 12 transmits the first surgical image signal to the IP converter 100 that is the third image processing device (Step S205). Thus, the IP converter 100 acquires the first surgical image signal. Note that Step S205 may be performed simultaneously with Step S204, or may be performed before Step S204.

The image processing server 20 performs the second image processing on the first surgical image signal (Step S206). Thus, the image processing server 20 generates the second surgical image signal obtained by performing the second image processing on the first surgical image signal.

Then, the image processing server 20 transmits the second surgical image signal to the IP converter 100 (Step S207). Thus, the IP converter 100 acquires the second surgical image signal.

Then, the IP converter 100 performs the third image processing by using the first surgical image signal and the second surgical image signal (Step S208). The IP converter 100 performs the third image processing on at least one of the first surgical image signal and the second surgical image signal, and generates the display image signal.

Then, the IP converter 100 transmits the display image signal to the image receiving device 200 (Step S209). Thus, the image receiving device 200 acquires the display image signal. Then, the image receiving device 200 displays the display image signal (Step S210).

[1-8. Arrangement Example of Component Elements of Medical Imaging System]

Figure 7:
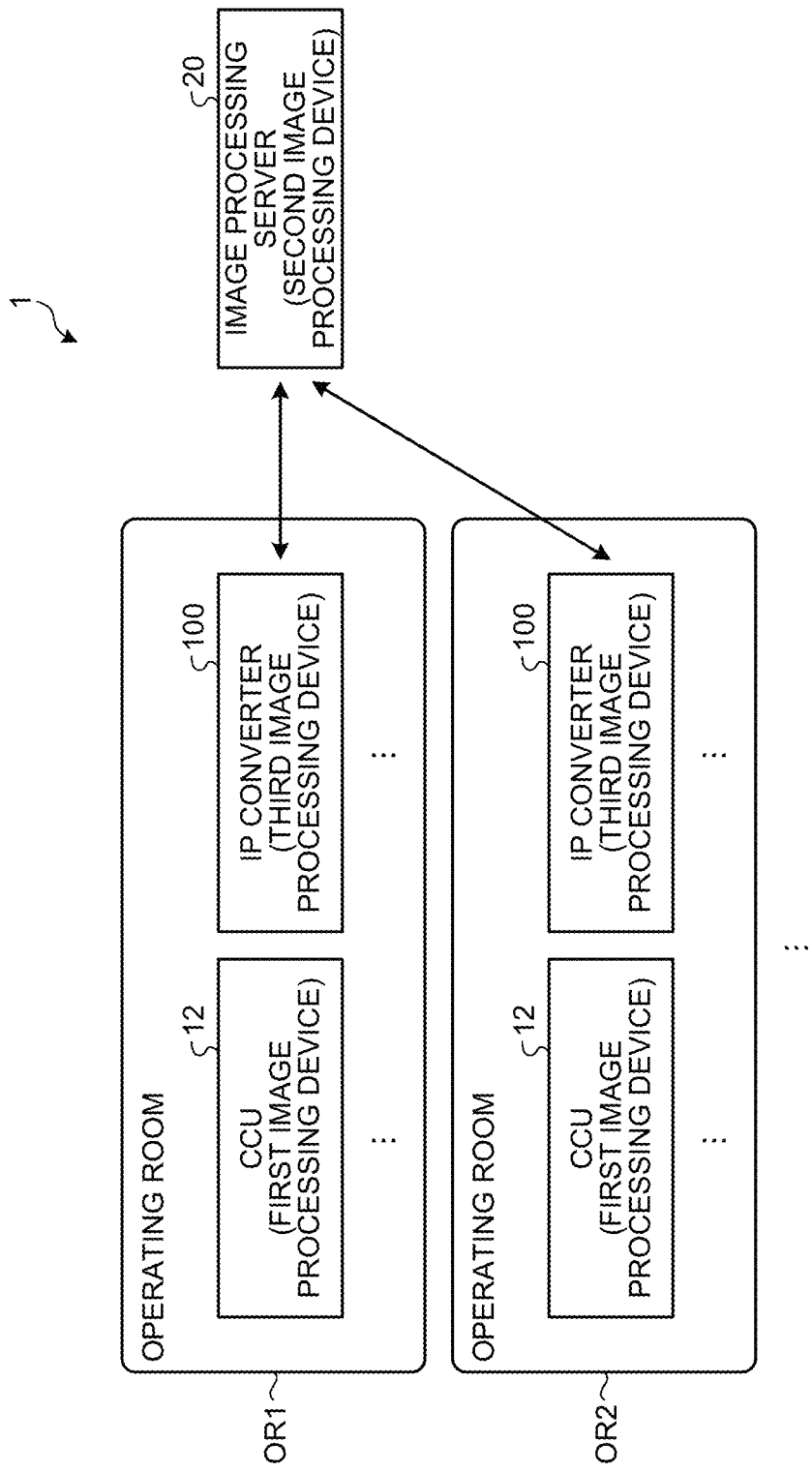
FIG. 7 is a diagram illustrating an example of arrangement of component elements of the medical imaging system.

The medical imaging system 1 illustrated in FIG. 7 will be described. FIG. 7 is a diagram illustrating an example of arrangement of the component elements of the medical imaging system.

As illustrated in FIG. 7, the medical imaging system 1 may have a configuration in which the CCUs 12 and IP converters 100 are each arranged in a plurality of operating rooms OR1 and OR2, and the like. The medical imaging system 1 may include one image processing server 20 that communicates with the IP converter 100 and the like arranged in each of the operating rooms OR1 and OR2. The image processing server 20 transmits and receives information to and from each of the CCUs 12 and IP converters 100 arranged in each of the plurality of operating rooms OR1 and OR2, and the like.

The IP converter 100 arranged in the operating room OR1 transmits and receives information to and from the image processing server 20 and the CCU 12 arranged in the operating room OR1. For example, the IP converter 100 arranged in the operating room OR1 acquires the first surgical image signal from the CCU 12 arranged in the operating room OR1. Furthermore, for example, the IP converter 100 arranged in the operating room OR1 acquires, from the image processing server 20, the second surgical image signal obtained by performing the second image processing on the first surgical image signal from the CCU 12 arranged in the operating room OR1.

As described above, the medical imaging system 1 may have a system configuration including one image processing server 20 and a plurality of IP converters 100 arranged in the plurality of operating rooms OR1 and OR2, and the like. The medical imaging system 1 may have a configuration that includes one second image processing device, a plurality of first image processing devices and third image processing devices, and the operating rooms each having arrangement of the first image processing device and third image processing device.

2. Other Embodiments

The processing according to the embodiments described above may be implemented in various different forms (modifications) in addition to the embodiments described above. The medical imaging system is not limited to the examples described above, and may have various forms. This point will be described below. Hereinafter, description of the same points as those of the IP converter 100 according to the embodiment will be omitted as appropriate.

[2-1. Modifications]

In the example described above, the camera 11 as the imaging device and the CCU 12 as the first image processing device that are separated have been described, but the camera and the CCU may be integrated with each other.

[2-2. Others]

Furthermore, in the processing having been described in the above embodiments, all or part of the processing described to be automatically performed can be performed manually, or all or part of the processing described to be performed manually can be performed automatically by a known method. In addition, the process procedure, specific names, and information including various data and parameters which are shown in the above descriptions or illustrated in drawings can be appropriately changed unless otherwise specified. For example, the various information illustrated in the drawings are not limited to the illustrated information.

Furthermore, the component elements of the devices are illustrated as functional concepts and are not necessarily required to be physically configured as illustrated. In other words, the specific forms of distribution or integration of the devices are not limited to those illustrated, and all or part thereof can be configured by being functionally or physically distributed or integrated, in any units, according to various loads or usage conditions.

Furthermore, the embodiments and modifications described above can be appropriately combined within a range consistent with the contents of the processing.

Furthermore, the effects described herein are merely examples and not limited thereto, and other effects may also be provided.

3. Effects According to Present Disclosure

As described above, the medical imaging system (the medical imaging system 1 in the embodiment) according to the present disclosure includes the imaging device (the camera 11 in the embodiment), the second image processing device (the image processing server 20 in the embodiment), and the third image processing device (the IP converter 100 in the embodiment). The second image processing device acquires the first surgical image signal that is the surgical image signal subjected to the first image processing by the first image processing device (the CCU 12 in the embodiment) performing the first image processing on the surgical image signal captured by the imaging device, and performs the second image processing on the first surgical image signal, and the third image processing device acquires the first surgical image signal and the second surgical image signal that is the surgical image signal subjected to the second image processing, performs the third image processing on at least one of the first surgical image signal and the second surgical image signal, and generates the display image signal by the conversion processing based on the first surgical image signal and the second surgical image signal, in which the first image processing, the second image processing, and the third image processing are different image processing.

In this configuration of the medical imaging system according to the present disclosure, the first image processing device performs the first image processing, the second image processing device performs the second image processing, the third image processing device performs the third image processing on at least one of the first surgical image signal and the second surgical image signal that are results of the processing, and the display image signal is generated As described above, the medical imaging system causes the three image processing devices to perform distributed different image processing. Therefore, the medical imaging system is allowed to appropriately generate an image to be displayed, by the image processing functions distributed to the respective devices.

In addition, the second image processing requires the amount of calculation larger than that required for the third image processing. This configuration makes it possible for the medical imaging system to cause the second image processing device different from the third image processing device to perform image processing requiring a large amount of calculation, thereby suppressing an increase in processing load on the third image processing device generating the display image signal. Therefore, the medical imaging system is allowed to appropriately generate an image to be displayed, by the image processing functions distributed to the respective devices.

Furthermore, the second image processing is image processing in which the amount of calculation changes depending on the content of the image to be processed. This configuration makes it possible for the medical imaging system to cause the second image processing device different from the third image processing device to perform the second image processing as the image processing in which the amount of calculation changes depending on the content of the image to be processed, thereby suppressing the change in processing load on the third image processing device generating the display image signal. Therefore, the medical imaging system is allowed to appropriately generate an image to be displayed, by the image processing functions distributed to the respective devices.

Furthermore, the first image processing device is the camera control unit (CCU), the third image processing device is the Internet Protocol (IP) converter, and the first image processing device and the third image processing device are arranged in the operating room. This configuration makes it possible to cause the second image processing device other than the CCU and the IP converter that are arranged in the operating room to perform the second image processing, thereby suppressing the increase in processing load on the devices arranged in the operating room. Therefore, the medical imaging system is allowed to appropriately generate an image to be displayed, by the image processing functions distributed to the respective devices.

Furthermore, the second image processing device is the server device that is arranged outside the operating rooms, and the second image processing device is connected to a plurality of IP converters arranged in different operating rooms. This configuration makes it possible to cause the server device that are arranged outside the operating rooms to perform the second image processing, thereby suppressing the increase in processing load on the devices arranged in the operating rooms. Therefore, the medical imaging system is allowed to appropriately generate an image to be displayed, by the image processing functions distributed to the respective devices.

In addition, the third image processing device performs the third image processing on the basis of a result of the second image processing by the second image processing device. This configuration makes it possible for the medical imaging system to perform the third image processing on the basis of the result of the second image processing. Thereby the third image processing is allowed to be performed with appropriate processing contents according to the second image processing to generate the display image signal. Therefore, the medical imaging system is allowed to appropriately generate an image to be displayed, by the image processing functions distributed to the respective devices.

Furthermore, the third image processing device performs the third image processing on the third surgical image signal obtained by superimposing the second surgical image signal on the first surgical image signal. This configuration makes it possible for the medical imaging system to perform the third image processing on the third surgical image signal obtained by superimposing the second surgical image signal on the first surgical image signal, thereby appropriately generating the display image signal. Therefore, the medical imaging system is allowed to appropriately generate an image to be displayed, by the image processing functions distributed to the respective devices.

Furthermore, the second image processing employs the simultaneous localization and mapping (SLAM) or the object recognition using the machine learning This configuration makes it possible for the medical imaging system to cause the second image processing device different from the third image processing device to perform the image processing requiring a large amount of calculation, such as the SLAM or the object recognition using machine learning, thereby suppressing the increase in processing load on the third image processing device generating the display image signal. Therefore, the medical imaging system is allowed to appropriately generate an image to be displayed, by the image processing functions distributed to the respective devices.

Furthermore, at least one of the first image processing device, the second image processing device, and the third image processing device performs processing on the basis of the control command acquired from the another device. This configuration makes it possible for the medical imaging system to appropriately control each image processing device. Therefore, the medical imaging system is allowed to appropriately generate an image to be displayed, by the image processing functions distributed to the respective devices.

Furthermore, the second image processing device includes the plurality of applications, and an application to be used is selected from the plurality of applications, according to the designation from the client terminal. This configuration makes it possible for the medical imaging system to cause the second image processing device to perform the processing according to the designation from the client terminal. Therefore, the medical imaging system is allowed to appropriately generate an image to be displayed, by the image processing functions distributed to the respective devices.

In addition, the third image processing device performs the third image processing based on the selected application, in response to the instruction from the client terminal. This configuration makes it possible for the medical imaging system to cause the third image processing device to perform the processing according to the designation from the client terminal. Therefore, the medical imaging system is allowed to appropriately generate an image to be displayed, by the image processing functions distributed to the respective devices.

In addition, the third image processing device changes the contents of the third image processing on the basis of the type of the second image processing. This configuration makes it possible for the medical imaging system to cause the third image processing device to appropriately perform the processing by changing the contents of the third image processing on the basis of the type of the second image processing. Therefore, the medical imaging system is allowed to appropriately generate an image to be displayed, by the image processing functions distributed to the respective devices.

In addition, when the second image processing device does not respond, the third image processing device sets the first surgical image signal as the display image signal. This configuration makes it possible for the medical imaging system to suppress non-generation of the display image signal, even if the second image processing device does not normally operate. Therefore, the medical imaging system is allowed to appropriately generate an image to be displayed, by the image processing functions distributed to the respective devices.

The image processing device (the IP converter 100 in the embodiment) according to the present disclosure includes the acquisition unit (the acquisition unit 131 in the embodiment) and the generation unit (the generation unit 133 in the embodiment). The acquisition unit acquires, from the medical imaging device including the imaging device and the first image processing device performing the first image processing on the surgical image signal captured by the imaging device, the first surgical image signal that is the surgical image signal subjected to the first image processing and the second surgical image signal that is the surgical image signal obtained by performing the second image processing on the first surgical image signal by the second image processing device, and the generation unit performs the third image processing on at least one of the first surgical image signal and the second surgical image signal and generates the display image signal by the conversion processing based on the first surgical image signal and the second surgical image signal, in which the first image processing, the second image processing, and the third image processing are different image processing.

Therefore, the image processing device according to the present disclosure generates the display image signal by performing the third image processing on at least one of the first surgical image signal obtained by performing the first image processing by the first image processing device and the second surgical image signal obtained by performing the second image processing by the second image processing device. As described above, the image processing devices each perform image processing different from the image processing distributed to and performed by the other image processing devices, and the display image signal is generated. Accordingly, the image processing devices are configured to appropriately generate the image to be displayed by the image processing functions distributed to the respective devices.

4. Hardware Configuration

Figure 8:
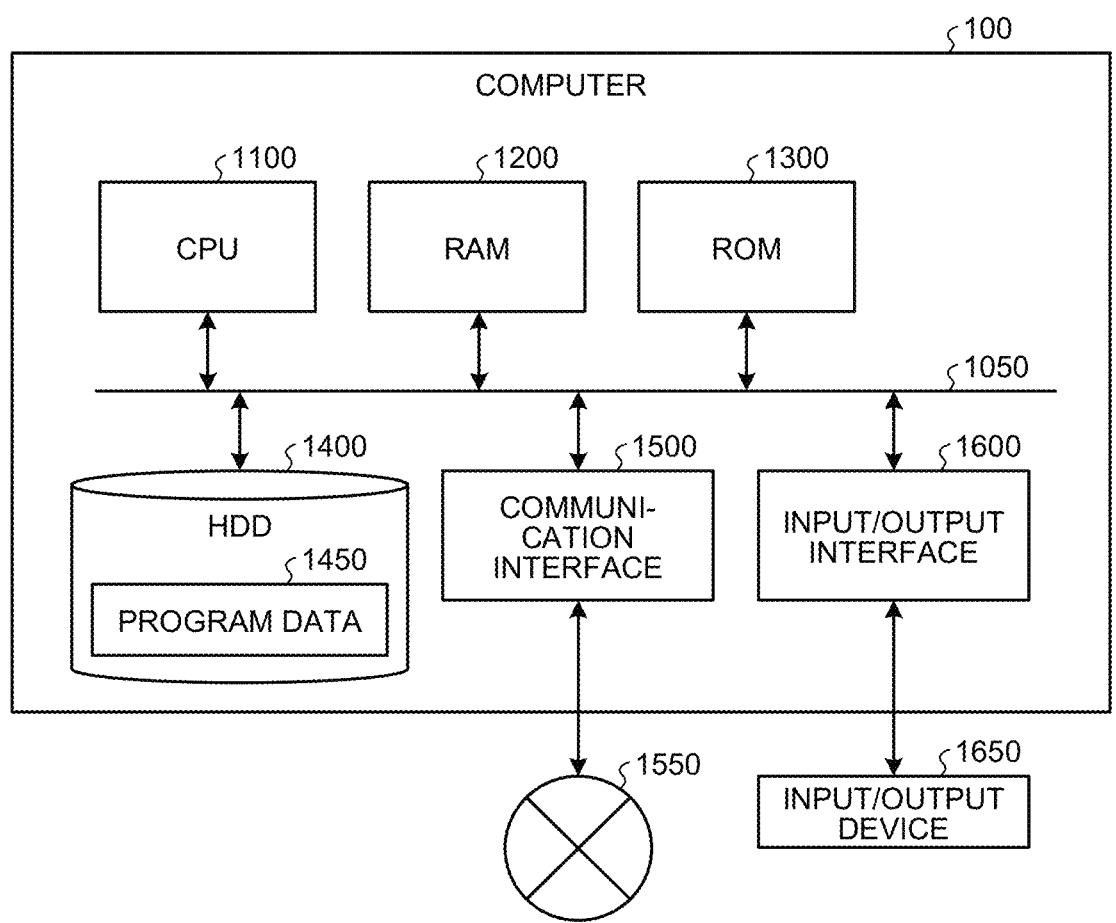
FIG. 8 is a hardware configuration diagram illustrating an example of a computer implementing functions of the image processing devices.

The image processing devices, such as the CCU 12 that is the first image processing device, the image processing server 20 that is the second image processing device, and the IP converter 100 that is the third image processing device, according to the embodiments and modifications thereof described above are implemented by, for example, a computer 1000 having a configuration as illustrated in FIG. 8. FIG. 8 is a hardware configuration diagram illustrating an example of the computer 1000 implementing the functions of the image processing devices (computers) such as the CCU 12, the image processing server 20, and the IP converter 100. Hereinafter, an example of the IP converter 100 according to the embodiment will be described. The computer 1000 includes a CPU 1100, a RAM 1200, a read only memory (ROM) 1300, a hard disk drive (HDD) 1400, a communication interface 1500, and an input/output interface 1600. The respective units of the computer 1000 are connected by a bus 1050.

The CPU 1100 is operated on the basis of programs stored in the ROM 1300 or the HDD 1400 and controls the respective units. For example, the CPU 1100 deploys the programs stored in the ROM 1300 or the HDD 1400 to the RAM 1200 and executes processing corresponding to various programs.

The ROM 1300 stores a boot program such as a basic input output system (BIOS) executed by the CPU 1100 when the computer 1000 is booted, a program depending on the hardware of the computer 1000, and the like.

The HDD 1400 is a computer-readable recording medium that non-transitorily records the programs executed by the CPU 1100, data used by the programs, and the like. Specifically, the HDD 1400 is a recording medium that records the image processing program (the image processing program or the like such as the third image processing program or the like) according to the present disclosure, the image processing program being an example of program data 1450.

The communication interface 1500 is an interface for connecting the computer 1000 to an external network 1550 (e.g., the Internet). For example, the CPU 1100 receives data from another device or transmits data generated by the CPU 1100 to another device, via the communication interface 1500.

The input/output interface 1600 is an interface for connecting an input/output device 1650 and the computer 1000. For example, the CPU 1100 receives data from an input device such as a keyboard or mouse via the input/output interface 1600. In addition, the CPU 1100 transmits data to an output device such as a display, speaker, or printer via the input/output interface 1600. Furthermore, the input/output interface 1600 may function as a media interface that reads a program or the like recorded on a predetermined recording medium. The medium includes, for example, an optical recording medium such as a digital versatile disc (DVD) or phase change rewritable disk (PD), a magneto-optical recording medium such as a magneto-optical disk (MO), a tape medium, a magnetic recording medium, a semiconductor memory, or the like. For example, when the computer 1000 functions as the IP converter 100 according to an embodiment, the CPU 1100 of the computer 1000 implements the functions of the control unit 130 and the like by executing an image processing program loaded on the RAM 1200. Furthermore, the image processing program according to the present disclosure and data in the storage unit 120 are stored in the HDD 1400. Note that the CPU 1100 reads the program data 1450 from the HDD 1400 and executes the program data, but in another example, the CPU 1100 may acquire the programs from the other devices via the external network 1550.

Note that the present technology can also employ the following configurations.

(1)

A medical imaging system comprising:
- a second image processing device that acquires a first surgical image signal being a surgical image signal subjected to first image processing, from a medical imaging device including an imaging device and a first image processing device performing the first image processing on the surgical image signal captured by the imaging device, and performs second image processing on the first surgical image signal; and
- a third image processing device that acquires the first surgical image signal and a second surgical image signal being a surgical image signal subjected to the second image processing, performs third image processing on at least one of the first surgical image signal and the second surgical image signal, and generates a display image signal by conversion processing based on the first surgical image signal and the second surgical image signal,
- wherein the first image processing, the second image processing, and the third image processing are different image processing.

(2)

The medical imaging system according to (1), wherein the second image processing requires an amount of calculation larger than that required for the third image processing.

(3)

The medical imaging system according to (1) or (2), wherein in the second image processing, an amount of calculation changes depending on a content of an image to be processed.

(4)

The medical imaging system according to any one of (1) to (3), wherein the first image processing device is a camera control unit (CCU), the third image processing device is an Internet Protocol (IP) converter, and the first image processing device and the third image processing device are arranged in an operating room.

(5)

The medical imaging system according to (4), wherein the second image processing device is a server device arranged outside the operating room, and the second image processing device is connected to a plurality of IP converters arranged in different operating rooms.

(6)

The medical imaging system according to any one of (1) to (5), wherein the third image processing device performs the third image processing based on a result of the second image processing by the second image processing device.

(7)

The medical imaging system according to any one of (1) to (5), wherein the third image processing device performs the third image processing on a third surgical image signal obtained by superimposing the second surgical image signal on the first surgical image signal.

(8)

The medical imaging system according to any one of (1) to (6), wherein the second image processing employs either simultaneous localization and mapping (SLAM) or object recognition using machine learning.

(9)

The medical imaging system according to any one of (1) to (8), wherein at least one of the first image processing device, the second image processing device, and the third image processing device performs processing based on a control command acquired from another device.

(10)

The medical imaging system according to any one of (1) to (9), wherein the second image processing device includes a plurality of applications, and an application to be used is selected from the plurality of applications by designation from a client terminal.

(11)

The medical imaging system according to (10), wherein the third image processing device performs the third image processing based on the selected application, in response to an instruction from the client terminal.

(12)

The medical imaging system according to any one of (1) to (11), wherein the third image processing device changes a content of the third image processing based on a type of the second image processing.

(13)

The medical imaging system according to any one of (1) to (12), wherein when the second image processing device does not respond, the third image processing device sets the first surgical image signal as the display image signal.

(14)

A medical imaging method, wherein a second image processing device acquires a first surgical image signal being a surgical image signal subjected to first image processing, from a medical imaging device including an imaging device and a first image processing device performing the first image processing on the surgical image signal captured by the imaging device, and performs second image processing on the first surgical image signal, wherein a third image processing device acquires the first surgical image signal and a second surgical image signal being a surgical image signal subjected to the second image processing, performs third image processing on at least one of the first surgical image signal and the second surgical image signal, and generates a display image signal by conversion processing based on the first surgical image signal and the second surgical image signal, and wherein the first image processing, the second image processing, and the third image processing are different image processing.

(15)

An image processing device comprising:

an acquisition unit that acquires, from a medical imaging device including an imaging device and a first image processing device performing first image processing on a surgical image signal captured by the imaging device, a first surgical image signal being a surgical image signal subjected to the first image processing, and further acquires a second surgical image signal being a surgical image signal obtained by performing second image processing on the first surgical image signal by a second image processing device; and a generation unit that performs third image processing on at least one of the first surgical image signal and the second surgical image signal, and generates a display image signal by conversion processing based on the first surgical image signal and the second surgical image signal, wherein the first image processing, the second image processing, and the third image processing are different image processing.

REFERENCE SIGNS LIST

1 MEDICAL IMAGING SYSTEM
10 MEDICAL IMAGING DEVICE
11 CAMERA
12 CCU (FIRST IMAGE PROCESSING DEVICE)
20 IMAGE PROCESSING SERVER (SECOND IMAGE PROCESSING
DEVICE)
100 IP CONVERTER (THIRD IMAGE PROCESSING DEVICE)
110 COMMUNICATION UNIT
120 STORAGE UNIT
130 CONTROL UNIT

131 ACQUISITION UNIT
132 DETERMINATION UNIT
133 GENERATION UNIT
134 TRANSMISSION UNIT
200 IMAGE RECEIVING DEVICE (MONITOR)

The invention claimed is:

1. A medical imaging system comprising:
a second image processing device that acquires a first surgical image signal being a surgical image signal subjected to first image processing, from a medical imaging device including an imaging device and a first image processing device performing the first image processing on the surgical image signal captured by the imaging device, and performs second image processing on the first surgical image signal; and
a third image processing device that acquires the first surgical image signal and a second surgical image signal being a surgical image signal subjected to the second image processing, performs third image processing on at least one of the first surgical image signal and the second surgical image signal, and generates a display image signal by conversion processing based on the first surgical image signal and the second surgical image signal,
wherein the first image processing, the second image processing, and the third image processing are different image processing.

2. The medical imaging system according to claim 1, wherein
the second image processing requires an amount of calculation larger than that required for the third image processing.

3. The medical imaging system according to claim 1, wherein
in the second image processing, an amount of calculation changes depending on a content of an image to be processed.

4. The medical imaging system according to claim 1, wherein
the first image processing device is a camera control unit (CCU),
the third image processing device is an Internet Protocol (IP) converter, and
the first image processing device and the third image processing device are arranged in an operating room.

5. The medical imaging system according to claim 4, wherein
the second image processing device is a server device arranged outside the operating room, and
the second image processing device is connected to a plurality of IP converters arranged in different operating rooms.

6. The medical imaging system according to claim 1, wherein
the third image processing device performs the third image processing based on a result of the second image processing by the second image processing device.

7. The medical imaging system according to claim 1, wherein
the third image processing device performs the third image processing on a third surgical image signal obtained by superimposing the second surgical image signal on the first surgical image signal.

8. The medical imaging system according to claim 1, wherein
the second image processing employs either simultaneous localization and mapping (SLAM) or object recognition using machine learning.

9. The medical imaging system according to claim 1, wherein
at least one of the first image processing device, the second image processing device, and the third image processing device performs processing based on a control command acquired from another device.

10. The medical imaging system according to claim 1, wherein
the second image processing device includes a plurality of applications, and
an application to be used is selected from the plurality of applications by designation from a client terminal.

11. The medical imaging system according to claim 10, wherein
the third image processing device performs the third image processing based on the selected application, in response to an instruction from the client terminal.

12. The medical imaging system according to claim 1, wherein
the third image processing device changes a content of the third image processing based on a type of the second image processing.

13. The medical imaging system according to claim 1, wherein
when the second image processing device does not respond, the third image processing device sets the first surgical image signal as the display image signal.

14. A medical imaging method,
wherein a second image processing device
acquires a first surgical image signal being a surgical image signal subjected to first image processing, from a medical imaging device including an imaging device and a first image processing device performing the first image processing on the surgical image signal captured by the imaging device, and performs second image processing on the first surgical image signal,
wherein a third image processing device
acquires the first surgical image signal and a second surgical image signal being a surgical image signal subjected to the second image processing, performs third image processing on at least one of the first surgical image signal and the second surgical image signal, and generates a display image signal by conversion processing based on the first surgical image signal and the second surgical image signal, and
wherein the first image processing, the second image processing, and the third image processing are different image processing.

15. An image processing device comprising:
an acquisition unit that acquires, from a medical imaging device including an imaging device and a first image processing device performing first image processing on a surgical image signal captured by the imaging device, a first surgical image signal being a surgical image signal subjected to the first image processing, and further acquires a second surgical image signal being a surgical image signal obtained by performing second image processing on the first surgical image signal by a second image processing device; and
a generation unit that performs third image processing on at least one of the first surgical image signal and the second surgical image signal, and generates a display image signal by conversion processing based on the first surgical image signal and the second surgical image signal,
wherein the first image processing, the second image processing, and the third image processing are different image processing.

* * * * *